US012616446B2

(12) United States Patent
Axelrod et al.

(10) Patent No.: US 12,616,446 B2
(45) Date of Patent: May 5, 2026

(54) WEARABLE GARMENT ADAPTED FOR ULTRASOUND SENSING AND METHODS THERETO FOR FULL WAVE INVERSION WITH IMPRECISE SENSOR POSITIONS

(71) Applicant: Ikko Health Ltd., Tel Aviv (IL)

(72) Inventors: Ramon Axelrod, Kiryat Ono (IL); Pinchas Chaviv, Hod Hasharon (IL)

(73) Assignee: Ikko Health Ltd., Tel Aviv (IL)

( * ) Notice: Subject to any disclaimer, the term of this patent is extended or adjusted under 35 U.S.C. 154(b) by 26 days.

(21) Appl. No.: 18/331,565

(22) Filed: Jun. 8, 2023

(65) Prior Publication Data

US 2023/0309960 A1 Oct. 5, 2023

Related U.S. Application Data

(63) Continuation of application No. PCT/IB2021/061474, filed on Dec. 8, 2021.

(60) Provisional application No. 63/123,159, filed on Dec. 9, 2020.

(51) Int. Cl.
*A61B 8/00* (2006.01)

(52) U.S. Cl.
CPC .......... *A61B 8/4427* (2013.01); *A61B 8/4254* (2013.01)

(58) Field of Classification Search
CPC ... A61B 8/4427; A61B 8/4254; A61B 8/4281; A61B 8/4494; A61B 8/4209; A61B 8/0866; A61B 8/0875; A61B 8/0883; A61B 8/4472; A61B 5/6804; A61B 5/6805
See application file for complete search history.

(56) References Cited

U.S. PATENT DOCUMENTS

| | | | |
|---|---|---|---|
| 5,598,845 A | 2/1997 | Chandraratna et al. |
| 6,213,958 B1 | 4/2001 | Winder |
| 6,243,599 B1 | 6/2001 | Horn |
| 6,261,237 B1 | 7/2001 | Swanson et al. |

(Continued)

FOREIGN PATENT DOCUMENTS

| | | |
|---|---|---|
| WO | 2018060456 A1 | 4/2018 |
| WO | 2019046550 A1 | 3/2019 |

(Continued)

OTHER PUBLICATIONS

A Fast Slam Approach to Freehand 3-D Ultrasound Reconstruction for Catheter Ablation Guidance in the Left Atrium, Ultrasound in Medicine & Biology vol. 37, Issue 12, Dec. 2011.

(Continued)

*Primary Examiner* — Peter Luong
(74) *Attorney, Agent, or Firm* — M&B IP Analysts, LLC

(57) ABSTRACT

A wearable sensing garment for sensing ultrasound waves from a body part is provided. The sensing garment includes a mesh of fabric adapted to be worn on at least a body part of a wearer; and a plurality of ultrasound sensors disposed on the mesh fabric, wherein each of the plurality of ultrasound sensors are adapted to detect ultrasound waves returned from the at least a body part of the wearer and further adapted to transmit at least portion of the detected ultrasound waves to a controller communicatively connected thereto, and wherein only a portion of the plurality of ultrasound sensors that is larger than a predetermined number of ultrasound sensors is substantially in contact with a skin layer of the at least a body part.

28 Claims, 7 Drawing Sheets

100

(56) References Cited

U.S. PATENT DOCUMENTS

| | | | |
|---|---|---|---|
| 6,478,739 | B1 | 11/2002 | Hong |
| 6,574,494 | B2 | 6/2003 | Horn |
| 6,699,201 | B2 | 3/2004 | Stearns |
| 6,937,893 | B2 | 8/2005 | Danz et al. |
| 6,984,208 | B2 | 1/2006 | Zheng |
| 8,155,729 | B1 | 4/2012 | Hsieh et al. |
| 8,235,907 | B2 | 8/2012 | Wilk et al. |
| 9,022,933 | B2 | 5/2015 | Hsieh et al. |
| 9,480,863 | B2 | 11/2016 | Lewis, Jr. et al. |
| 10,028,728 | B2* | 7/2018 | Huang ................. A61B 8/4477 |
| 10,238,362 | B2 | 3/2019 | Lahiji et al. |
| 10,610,193 | B2 | 4/2020 | Bar-Zion et al. |
| 10,667,795 | B2 | 6/2020 | Ensenaliev |
| 10,702,243 | B2 | 7/2020 | Yang et al. |
| 10,792,011 | B2 | 10/2020 | Toume et al. |
| 10,813,620 | B2 | 10/2020 | Owen et al. |
| 11,064,924 | B2 | 7/2021 | Woltjer et al. |
| 2005/0020918 | A1* | 1/2005 | Wilk ......................... A61B 8/00 600/439 |
| 2005/0020921 | A1* | 1/2005 | Glassell ................. A61B 8/085 600/463 |
| 2008/0021309 | A1 | 1/2008 | Amiot et al. |
| 2010/0280416 | A1* | 11/2010 | Hyde ..................... A61B 5/103 600/587 |
| 2011/0218423 | A1* | 9/2011 | Hsieh ..................... A61B 34/20 600/459 |
| 2014/0058263 | A1 | 2/2014 | Baym et al. |
| 2014/0163375 | A1 | 6/2014 | Wasielewski et al. |
| 2017/0080255 | A1 | 3/2017 | Law et al. |
| 2017/0354372 | A1 | 12/2017 | Varadan et al. |
| 2019/0328355 | A1 | 10/2019 | Calderon |
| 2020/0121281 | A1 | 4/2020 | Dagdeviren et al. |
| 2020/0163647 | A1 | 5/2020 | Hakkens et al. |
| 2020/0253491 | A1 | 8/2020 | Nurmikko |
| 2020/0289087 | A1 | 9/2020 | Beckers et al. |
| 2021/0093291 | A1 | 4/2021 | Sanchez |
| 2021/0138275 | A9 | 5/2021 | Kabrams et al. |
| 2021/0169443 | A1 | 6/2021 | Shurtliff et al. |
| 2021/0215642 | A1* | 7/2021 | Fincke ................... G01N 33/12 |

FOREIGN PATENT DOCUMENTS

| | | | |
|---|---|---|---|
| WO | 2019158350 | A1 | 8/2019 |
| WO | 2020165383 | A1 | 8/2020 |

OTHER PUBLICATIONS

Frequency Dependence on Ultrasound Attenuation and Backscatter in Breast Tissue, Ultrasound in Med. & Biol. vol. 12, No. 10, pp. 795-808, 1986.

International Search Report and Written Opinion for PCT/IB2021/061474, dated Mar. 16, 2022. International Bureau of WIPO.

Pérez-Liva, M., et al. "Time Domain Reconstruction of Sound Speed and Attenuation in Ultrasound Computed Tomography Using Full Wave Inversiona)." The Journal of the Acoustical Society of America, vol. 141, No. 3, 2017, pp. 1595-1604, https://doi.org/10.1121/1.4976688.

Extended European Search Report for EP 21902838.8, dated Dec. 16, 2024. European Patent Office, Munich, Germany.

Communication pursuant to Rule 164(1) EPC, Supplementary Partial European Search Report for EP 21902838.8, dated Sep. 11, 2024. European Patent Office, Munich, Germany.

He X, Liu W, Chen S, Qin Z. A new approach to compensate the geometric distortion in the synthetic aperture ultrasonic imaging system. Biomed Mater Eng. 2015;26 Suppl 1:S1623-32. doi: 10.3233/BME-151461. PMID: 26405927. (Year: 2015).

Muji, et al, Optical tomography hardware development for solid gas measurement using mixed projection, Flow Measurement and Instrumentation, vol. 33, 2013, pp. 110-121, ISSN 0955-5986 (Year: 2013).

Notice of Reasons for Refusal for JP application 2023-535908, dated Sep. 16, 2025. Japan Patent Office, Tokyo, Japan.

* cited by examiner

160

410 ─ Processing Element

420 ─ Memory

470 ─ CIU

460 ─ PCU

430 ─ SCI

440 ─ ECI

450 ─ MCI

Emitter 1

Emitter 2

Trajectory of min. time signal

True Receiver

Area of uncertainty

WEARABLE GARMENT ADAPTED FOR ULTRASOUND SENSING AND METHODS THERETO FOR FULL WAVE INVERSION WITH IMPRECISE SENSOR POSITIONS

CROSS-REFERENCE TO RELATED APPLICATIONS

This application is a continuation of International Application No. PCT/IB2021/061474 filed on Dec. 8, 2021, which claims the benefit of U.S. Provisional Application No. 63/123,159 filed on Dec. 9, 2020. The contents of the above-referenced applications are hereby incorporated by reference.

TECHNICAL FIELD

The present disclosure generally relates to ultrasound imaging system and more particularly to wearable ultrasound sensors and the positioning determination thereof.

BACKGROUND

Ultrasound is commonly used for a variety of applications, including that of scanning non-invasively and at low-risk body parts. In a typical application, an array of ultrasound sensors is mounted on a flat surface. The body part to be scanned is coated with a gel to ensure better matching between the surface of the sensors and the skin of the body part. One or more emitters emit ultrasound waves in a desired frequency and the reflected or refracted sound waves are captured by the array of sensors. The signals are then interpreted to provide an image of the internal organs and bones of the body part. In a typical setting a patient is placed in a desired position to enable the use of the ultrasound array of sensors by a practitioner. Over time ultrasound imaging capabilities have improved and from images that only expert interpreters could decipher, it is possible today to provide three-dimensional imaging, which is evident, for example, when scanning a fetus in the womb with 3D details.

A drawback of an ultrasound array of sensors is that these are typically small in surface area and therefore when larger areas of the body need to be checked, the array has to be manually or automatically moved upon the patient's skin in order to reach the required coverage. Moreover, adequate contact between the ultrasound array of sensors and the patient's skin is required for effective and indisputable imaging results.

While prior art solutions suggest techniques to tackle some of these challenges, most often are deficient in achieving both and/or limited to specific applications. For example, one prior art solution directed at bone tissues suggests the use of an array of wideband emitter sensors and a wideband recorder. Although naturally wideband signals were measured, the sensor array was limited to analysis of bone tissues. Other prior art solutions targeted at, for example, breast tissue and fetal heart provide techniques to image larger areas of the patient at a single time. Yet, such example solutions are tailored to specific applications and further, require particular arrangements for sufficient contact necessary for ultrasound imaging. Even when ultrasound sensor array solutions are provided for a more general application, often, other imaging techniques such as computed tomography (CT) or magnetic resonance imaging (MRI) are operated in conjunction for more accurate results.

A key aspect of a wearable ultrasound apparatus requires adaptation to the body curvatures and more so, the changes thereof as a person moves and breathes, which in return, changes the relative location of the sensors. To this end, an ultrasound sensor array and technique that is geared at general applications and provides necessary contact is highly desired. In furtherance to the above, an ultrasound sensor and/or sensor arrays that removes inflexible, inconvenient, or discomfort when wearing, is needed.

It would therefore be advantageous to provide a wearable ultrasound sensing solution that overcomes the limitations of the prior art.

SUMMARY

A summary of several example embodiments of the disclosure follows. This summary is provided for the convenience of the reader to provide a basic understanding of such embodiments and does not wholly define the breadth of the disclosure. This summary is not an extensive overview of all contemplated embodiments, and is intended to neither identify key or critical elements of all embodiments nor to delineate the scope of any or all aspects. Its sole purpose is to present some concepts of one or more embodiments in a simplified form as a prelude to the more detailed description that is presented later. For convenience, the term "some embodiments" or "certain embodiments" may be used herein to refer to a single embodiment or multiple embodiments of the disclosure.

Certain embodiments disclosed herein include a sensing garment for sensing ultrasound waves from a body part. The sensing garment comprises: a mesh of fabric adapted to be worn on at least a body part of a wearer; and a plurality of ultrasound sensors disposed on the mesh fabric, wherein each of the plurality of ultrasound sensors are adapted to detect ultrasound waves returned from the at least a body part of the wearer and further adapted to transmit at least portion of the detected ultrasound waves to a controller communicatively connected thereto, and wherein only a portion of the plurality of ultrasound sensors that is larger than a predetermined number of ultrasound sensors is substantially in contact with a skin layer of the at least a body part.

Certain embodiments disclosed herein also include a system for determining locations of ultrasound sensors disposed onto a sensing garment, the sensing garment adapted to be positioned on at least a body part of a wearer such that at least a portion a plurality of the ultrasound sensors is substantially in contact with a skin layer of the at least a body part. The system comprises: a processing unit; a first interface, connected to the processing unit, the first interface adapted to provide communication to a plurality of ultrasound sensors disposed on a sensing garment; and a memory, the memory containing instructions that, when executed by the processing unit, configure the system to: perform at least determination of a position of at least a portion of the plurality of ultrasound sensors in relation to at least a body part.

BRIEF DESCRIPTION OF THE DRAWINGS

The subject matter disclosed herein is particularly pointed out and distinctly claimed in the claims at the conclusion of the specification. The foregoing and other objects, features, and advantages of the disclosed embodiments will be apparent from the following detailed description taken in conjunction with the accompanying drawings.

DETAILED DESCRIPTION

Figure 1:
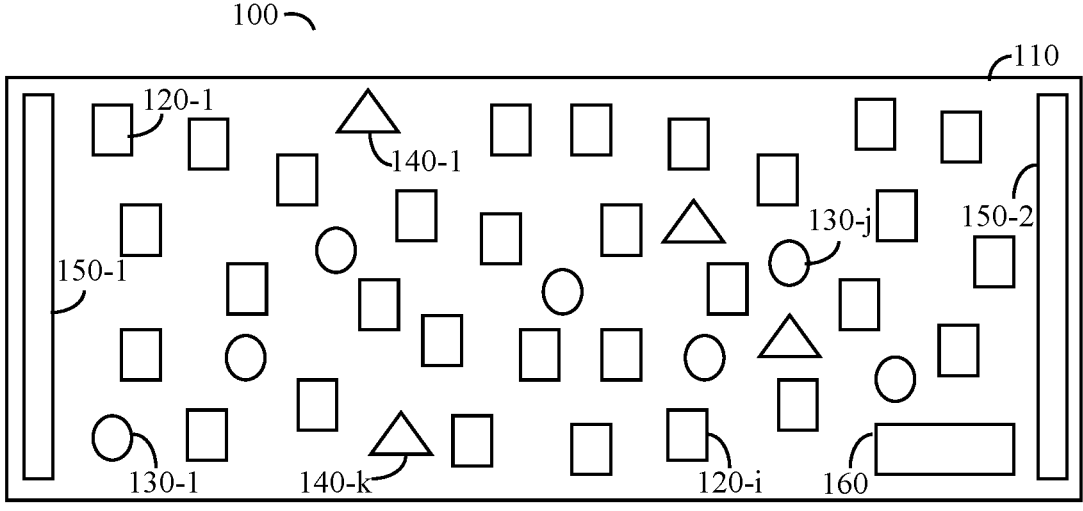
FIG. 1 is a schematic diagram of an ultrasound sensing garment with embedded sensors, emitters, and markers according to an embodiment.

It is important to note that the embodiments disclosed herein are only examples of the many advantageous uses of the innovative teachings herein. In general, statements made in the specification of the present application do not necessarily limit any of the various claimed embodiments. Moreover, some statements may apply to some inventive features but not to others. In general, unless otherwise indicated, singular elements may be in plural and vice versa with no loss of generality. In the drawings, like numerals refer to like parts through several views.

By of example to the disclosed embodiments, a wearable garment is embedded with a plurality of ultrasound sensors. The ultrasound sensors are adapted to collect signals emitted by a plurality of ultrasound emitters randomly or deliberately embedded into the wearable garment. A plurality of passive or active markers are positioned randomly or deliberately embedded at points on the garment to allow for determining specific ultrasound returns that cannot be contributed to bodily returns. The plurality of ultrasound sensors, markers, when applicable, and emitters, are communicatively connected to a controller that may be mounted to or otherwise embedded in the wearable garment. The controller is adapted to determine, on its own, or by sending signals to another unit, the position of the sensors and mapping them with respect to the body parts based on returned soundwaves collected by the sensors, using adaptations of full wave inversion (FWI) and simultaneous localization and mapping (SLAM).

FIG. 1 depicts an example schematic diagram 100 of an ultrasound sensing garment (USG) 110 disposed with sensors 120, emitters 130, and markers 140 embedded therein according to an embodiment. Embedding of sensors 120, emitters 130, and markers 140 may be achieved by different techniques such as, but not limited to, weaving, gluing, or mechanically attaching. The USG 110 is designed to provide an imaging solution that transmits and receives ultrasound signals that are then processed to generate a high-resolution, three dimensional (3D), image of a scanned body part. In an embodiment, power supply may be provided to elements embedded into the USG 110 may be provided by a mesh of conducting wires that are part of the USG 110. It should be further appreciated that the USG 110 may be shaped in various ways to be worn on a body part or parts, or otherwise wrapped thereabout. In one embodiment the USG 110 is designed to simply be laid upon a body part rather than be worn on the body part or wrapped around the body part. In one embodiment, one or more of the elements embedded into the USG 110 (i.e., sensors 120, emitters 130, and/or markers 140) may be coated with a soft, polymer-based material, allowing for sufficient contact, essentially without air gaps, between the element and the body part it is adjacent to. In yet another embodiment, the garment material is elastic and adapted to tightly correspond to the contour of the body part.

The USG 110 is further designed to comfortably fit about a body part having the necessary flexibility otherwise not provided by prior art solutions. This is achieved by avoiding the need for sensor arrays discussed in the related art. That is, sensor arrays that are typically big to give the wearable device a rigid feeling to it. Instead, miniature ultrasound sensors 120, for example, sensors 120-1 through 120-*i*, where 'i' is an integer greater than '1', the ultrasound sensors 120 also referred to herein simply as sensor 120, are configured on the USG 110. The sensors 120 are randomly or orderly embedded within the USG 110 and as their size, unlike an array of sensors, is small, the garment retains a flexible feel to it. According to an embodiment, and unlike prior art solutions, there is no need for the sensors 120 to be abutted to each other, and each sensor may be positioned upon the USG 110 as may be deemed necessary, maintaining a distance from one another. It may be referred to as a loose array as each sensor 120 is separate from any neighboring sensor. The miniature sensors 120 may be, but are not limited to, piezo-electric sensors, capacitive microelectromechanical systems (MEMS) based sensors, or capacitive polymer-based sensors.

In addition to the sensors 120, USG 110 also includes small ultrasound emitters 130, referred to herein also as emitters 130, for example emitter 130-1 through 130-*j*, where 'j' is an integer greater than '1'. The emitters 130 required for this solution are small emitters, and create a wide-angle beam in contrast with those used in prior art ultrasound solutions that are designed to create a tight beam. A small emitter is similar to the well-known problem of waves passing through a small aperture (or single slit or in the 2D case). Basically, each point on aperture is treated as a wave source and the intensity is calculated as a function of angle. The first minimum of intensity can be found from the equation:

$$d * \sin(\theta) = \lambda \tag{1}$$

where: $\lambda$ is the wavelength, d is the slit diameter, and $\theta$ is the angle from the perpendicular to an emitter, for example an emitter 130. The spread angle of the beam emitted can therefore be found to be:

$$\text{cone} = 2 * \text{asin}(\lambda/d) \tag{2}$$

Equation (2) may therefore be used to determine the spread angle, or cone, in various cases. For an echo ultrasound at a frequency of 15 MHz, $\lambda$=0.1 mm, d=20 mm and therefore the resultant cone is of 0.5°. Using regular full wave inversion (FWI) at 1.5 MHz, uses a small emitter with λ=1 mm, d=1 mm resulting in a cone of 90°, providing an advantage over the prior art. Clearly, the prior art relying on echo-based ultrasound scanning cannot provide the benefits disclosed herein. More details regarding the FWI operation according to embodiments are provided herein.

The USG 110 further includes markers 140, for example markers 140-1 through 140-k, where 'k' is an integer greater than or equal to '1'. The markers 140 are used to obtain an initial approximate position of the emitters 130 and sensors 120. The operation is discussed in greater detail herein.

Figure 2:
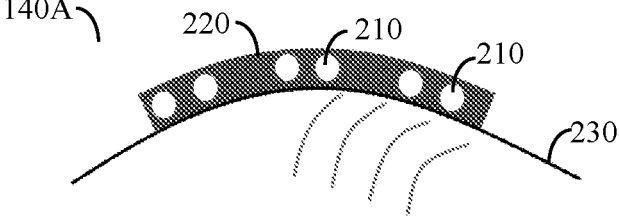
FIG. 2 is a cross-section of a first embodiment of markers according to an embodiment.

According to some embodiments, there are several solutions for these markers 140. The advantage of using markers 140 over other locating techniques is that the markers 140 do not hinder the movement and operational flexibility of the USG 110. This allows for a continuous use, including but not limited to real-time use, of the USG 110, providing its advantages over prior art solutions. In one embodiment, shown for example in FIG. 2, a cross-section of a marker 140A is made of several small metallic spheres 210 embedded in a flexible material 220, the material being, for example and without limitation, a plastic substance. The stretching or bending of it about a surface 230 causes the distance of metallic spheres 210 to change and so the returned waves differ. In an embodiment, the metallic spheres form a pattern that is easily detectable by processing of the returned ultrasound signals. The pattern is detectable when an emitter 130 or sensor 120 are far from the normal of the surface 230.

Figure 3A:
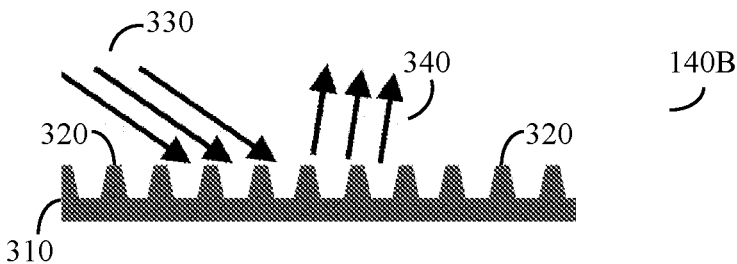
FIG. 3A is a cross-section of a second embodiment of markers in a flat position according to an embodiment.
Figure 3B:
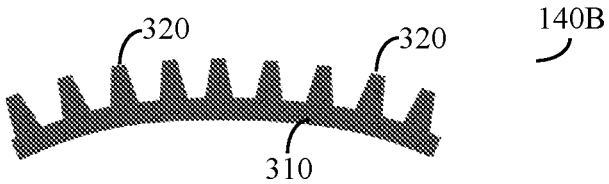
FIG. 3B is a cross-section of a second embodiment of markers in a bent position according to an embodiment.

In another example, shown in FIGS. 3A and 3B, a marker 140B comprises a flexible patch 310 comprising a grating 320 with a period of order similar to the ultrasound wavelength. In an embodiment, the size of such a flexible patch 310 is approximately 2 cm². The grating 320 of the flexible patch 310 causes incident waves 330 to be reflected 340 more in a certain direction than in other directions depending on the period. The period itself changes due to stretching and bending of the body part. In effect, the grating 320 may allow for higher sensitivity to the detection of the stretching and/or bending of the patch 310. Prior art solutions require external sources to identify the positions of the emitters 130 and/or sensors 120 and therefore fall short of the disclosed embodiments provided herein. In an embodiment, the markers 140 may be active markers that transmit a signal upon a trigger.

In an embodiment, the USG 110 may be further configured with fasteners 150 adapted to secure the USG 110 around a body part. The fasteners 150, for example fasteners 150-1 to 150-2, may comprise of hooks, Velcro®, buttons, and corresponding button loops or holes, and other solutions designed for such purpose. In an embodiment, the USG 110 may be further equipped with an electronic circuit 160 that is adapted to provide the power for consumption by the elements (sensors 120, emitters 130, and/or markers 140) embedded into the USG 110. Furthermore, the electronic circuit 160 may include a combination of digital, analog, and optical components as may be necessary for the proper operation of the USG 110. The signals received from the sensors 120 may be processed by the electronic circuit 160 locally or, after initial or minimal processing, transmitted, by wire or wirelessly to a processing device (not shown) that may further process the signal and display on a display device (not shown) an image corresponding to the processed signals.

Figures 4, 5:
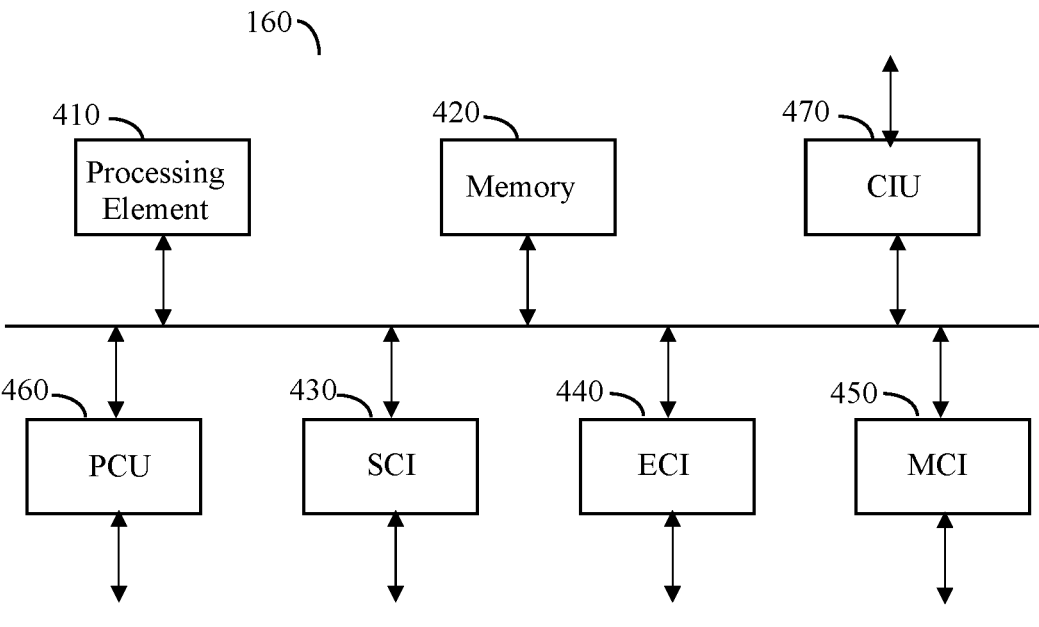
FIG. 4 is a block diagram of an electronic circuit for operation of the ultrasound sensing garment according to an embodiment.
FIG. 5 is a diagram describing a principle of operation of the ultrasound sensing garment according to an embodiment.

FIG. 4 depicts an example of an electronic circuit 160 according to an embodiment. A processing element (PE) 410 is communicatively connected to a memory 420. At least a portion of the memory 420 contains therein instructions that when executed by the PE 410 enable the USG 110 to perform the functions described herein. A sensor control interface (SCI) 430, communicatively connected to the PE 410, is adapted to at least receive from the sensors 120 signals that are sensed by the sensors 120. The SCI 430 may receive signals in parallel from all, part, or just one of the sensors 120. An emitter control interface (ECI) 440, communicatively connected to the PE 410, is adapted to at least send to the emitters 130 control signals to activate the emitters 130. The ECI 440 may transmit signals in parallel to all, part, or just one of the emitters 130.

In an embodiment, an optional marker control interface (MCI) 450, communicatively connected to the PE 410, may be used for active markers 140, and is adapted to at least activate the active markers 140. The MCI 450 may transmit control signals in parallel to all, part, or just one of the active markers 140. A power control unit (PCU) 460, connected to the PE 410, is configured to provide the necessary operational power to any required element of the USG 110 which can be performed in parallel, part, or just a single element of the USG 110.

In addition, a communication interface unit (CIU) 470 is communicatively connected to the PE 410, and is configured to provide communications to and from the USG 110. For example, and without limitation, it may provide: a) communication means to activate the USG 110; b) receive signals from an external device (not shown) controlling the USG 110; and c) transmit processed or raw signals captured by the sensors 120 according to any of the embodiments described herein. In one embodiment of the electronic circuit 160, the PE 410 and the memory 420 are replaced by, for example and without limitation, a combinational logic circuitry adapted to perform the tasks discussed herein. Such and similar embodiments are to be considered within the scope of the disclosed embodiments.

According to principles of the disclosed embodiments, a novel way to perform FWI with simultaneous localization and mapping (SLAM), and thus improve FWI initial sensor location identification, is now described. FWI is a method for high-resolution velocity models below a surface by means of ultrasound waves. The accuracy is gained by using the full wave-form acquired by simple sensors rather than return echoes which are possible only from complex array sensors. Given an initial model and emitter signals, the FWI method solves the wave equation to find the expected signal at the sensors for that model. It then iteratively updates the model to decrease the misfit between calculated and actually acquired signals.

Current FWI algorithms rely on accurate knowledge of the emitter and sensor positions and require an elaborate setup or cumbersome machines (using fixed, premeasured positions) limiting the use of standard FWI for industrial and medical applications. Algorithms for simultaneously locating the sensor position and mapping exist for other imaging technologies but cannot be trivially adapted to FWI as they rely on signal locality and signals travelling in a straight line.

It should be appreciated that a FWI signal processing comprises three components. First, a "forward pass" in which an elastic wave equation is used to find the expected signals at the sensors given the signal emitted and some assumed model. Second, a "backwards pass" in which the difference between the calculated and observed sensor signal is propagated backwards in time to find the required changes in the model parameters. Third, an optimizer that iteratively changes the model parameters to decrease the difference between observed and computed sensor signals. The forward pass connecting model and resulting waves can be denoted as:

$$u_i = F(x_e, m_i) \text{ with } s_k^i = u_k(x_k) \qquad (3)$$

The backwards pass takes the form:

$$\frac{\partial m_i}{\partial c} = B\left(m_i, u_i, \{\bar{s}_k^{obs}, s_k^i\}\right) \qquad (4)$$

Where: i—denotes the number of iteration (with corresponding assumed model $m_i$); $u_i$—is the wave solution resulting from emitter at $x_e$ and model $m_i$ (model at iteration i);

$$s_k^i$$

—is the computed signal from the kth sensor at iteration i;

$$\bar{s}^{obs} = \bar{s}_k^{obs}$$

—is the measured signal for the various sensors; $x_e$, $x_k$—denote the location of the emitter and kth sensor respectively; and, $m_i$—is the model at iteration i. The sound propagation velocity c(x) and attenuation through each point in the problem space and corresponding boundary conditions.

SLAM is a process in which a model is generated while simultaneously determining the location of sensors. It is used in photography and lidar (light-based radar) using an iterative process having three steps: a) a single sparse point cloud is generated from each couple (or more) of images captured using stereo disparity and feature matching. These results in multiple clouds which are not aligned; and, b) the different clouds are aligned and the transformation between them is found, (c) the location of cameras is updated resulting in a better alignment fit between the clouds.

According to one embodiment, modified forward and backward operators of the FWI equations (3) and (4) may include inaccuracy and change in sensor and emitter location. As a result, in each iteration, both the model and the sensor positions are updated:

$$\text{Forward: } u_i = F\left(x_e^i, m_i\right) \text{ with } s_k^i = u_k\left(x_k^i\right) \qquad (5)$$

$$\text{Backward: } \frac{\partial m_i}{\partial c} = B(m_i, u_i, \{\bar{s}_k\}), \nabla x_k^i = B'(m_i, u_i, \{\bar{s}_k\}) \qquad (6)$$

Where:

$$x_e^i \text{ and } x_k^i$$

are the assumed locations of the emitter and kth sensor respectively. It should be appreciated that such an approach works well when the hypothesized model $m_i$ and sensor positions are "close" to the true model and true positions and the need is just to improve the model. The challenge is that the FWI solution is not fully determined; and more than one solution may be possible because an error in sensor location can be offset by changing the sound velocity near it. Therefore, the optimization method may lead to a wrong local minimum. To overcome such potential deficiency, a loop is performed that contains a few steps of updating the model followed by a few steps of updating the position.

It should be appreciated that the results can be improved by modifications to the FWI operation. The FWI can be constrained in two ways: a) adding terms to the loss functions; and, b) constraining the trajectory of the optimization search. The loss term is more convenient for preventing certain local artifacts that arise in first approach described hereinabove for FWI and SLAM combination, in the case where the solution converges to a wrong local minimum of the sensors and/or emitters location.

According to an embodiment, a first possible way to improve results is to add a regularization term to prevent regions close to the sensors and emitters from changing rapidly compared to further regions. Since further regions are "seen" by many more sensors this prevents many local minima. According to another embodiment, a second possible way to improve the results is to analyze the signals prior to the FWI to find global constraints on sensors locations. These constraints can be used to solve for (imprecise) initial locations and also be incorporated in the FWI itself. For example, the time from signal emission to the first time it was received may be measured so as to constrain the possible distance between them.

Another type of artifact is a slight change in density along the lines between sensors and emitters (in essence these "offset" the error in distance between pairs without affecting other pairs). That is, the gradient of the density on points near the straight line is orthogonal (or rather closer to it) and the density rises more abruptly than points far from it. Therefore, a term is added that raises the loss if such gradients exist along the lines. Though, theoretically, there may always be a true surface along the line (i.e., the inspected model has an abrupt jump in density along that line), in the human body, most surfaces are curved. It should therefore be appreciated that a weighting coefficient that is low enough so that artifacts are removed but real surfaces are slightly smeared is used.

It should be further appreciated that a second change is made to the classical loss function where non-equal weighting of the difference between observed and simulated signals at the sensors is used. When emitters do not work simultaneously and broadcast in sufficiently spaced intervals, each signal received at the sensors, for example sensors 120, can be associated with one of the emitters, for example emitters 130. This allows weighting of the signals in a regression-like loss function of the FWI according to the distance between a sensor and emitter pair that is associated with a signal. The loss term can be defined as follows:

$$\text{loss} = \qquad (7)$$

$$\sum_{k,e} \int W_1(x_k, x_e)\left(s_{k,e}^{obs} - s_{k,e}\right)^2 dt + \sum_{k,e} \int W_2 L(x_k, x_e, \nabla m) dx + R(...)$$

Where, $W_1$ is the weighting of the regression term; $W_2$ is the weighting of the artifact along a straight-line term given by the function L; and, the third terms R(..) stands for standard regularization terms that limit the derivative in the model or constrain it to some prior knowledge of the model.

According to an embodiment, localization improvement is achieved by using global methods. As explained herein, FWI and SLAM use local optimization, typically variants of steepest descent, to improve the model and sensors localization. As such they are sensitive to the initial conditions, especially sensor locations. Therefore, various global methods are employed to improve the starting locations of the sensors. These methods assume some minimal knowledge of the model and add constraints onto the sensors', for example sensors 120, locations. Then a global solver is used to find the initial locations. While the examples herein pertain to ultrasound employed onto the human body, they should not be viewed as limiting upon the scope of the disclosed embodiments.

Specifically, it is known that the speed of sound in most soft tissue ranges between 1450 m/s (fat) to approximately 1570 m/s (liver) and 3000 m/s in bone. It is further known that the distance between an emitter and a sensor ranges from a few centimeters to approximately 0.4 meters (e.g., opposite sides of the abdomen or the skull). The relatively small variation in sound speed through soft tissue means that the minimal time trajectory between emitter and sensor does not deviate much from a straight line and the distance can be estimated from the signal travel time. For an actual distance of 0.5 meter between source (emitter) and target (sensor) the uncertainty reported by the literature is 7 millimeters (see FIG. 5). While a full wave form from an almost point source does not travel in a straight line like a ray, it is nevertheless correct for the start of the signal and when emitter and senor are far enough. The use of multiple emitters does not change the imprecision by much as the reason for uncertainty is not due to randomness. Having closer sensors can improve position detection, but because transmitters have a limited transmit angle this requires multiple sensors facing multiple directions at each position. Therefore, in practical deployments, solving for multiple sensors and taking into account a rough human model, the overall uncertainty of all sensors is approximately 4 millimeters.

Figure 6:
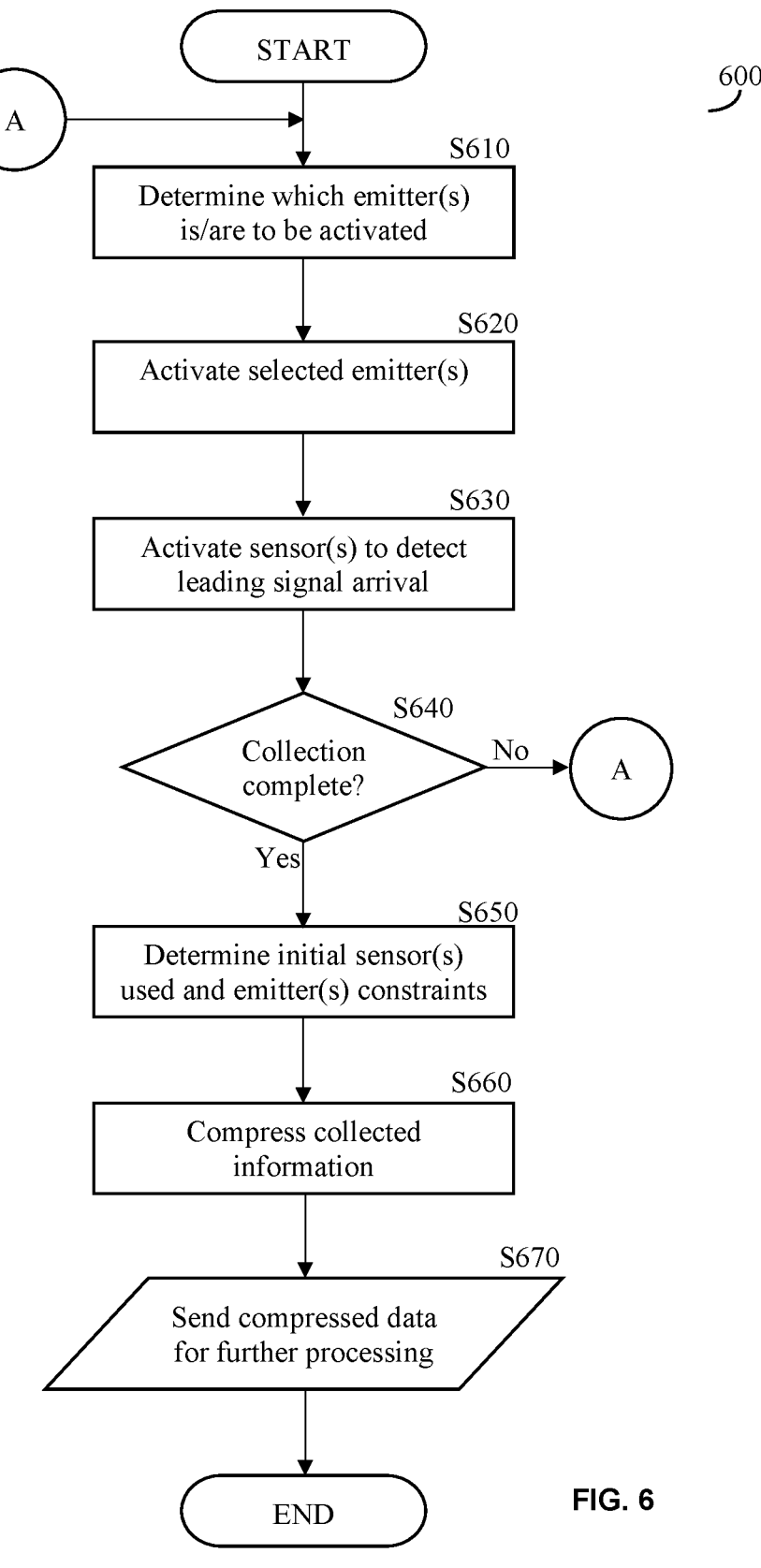
FIG. 6 is a flowchart illustrating a method of initial localization according to an embodiment.

FIG. 6 is an example flowchart 600 illustrating a method of initial localization according to an embodiment. The method will be described with reference to the elements shown in FIG. 1.

At S610, emitter(s) 130 of the USG 110 to activate for the process of initial localization is determined. The process may require the actuation of one or more of the emitters 130 simultaneously. The process may further make use of one or more of the markers 140 as described herein.

At S620, the selected one or more emitters 130 of the plurality of emitters on USG 110 are activated. That is, the selected emitters 130 begin sending the ultrasound signals. At S630, one or more sensors 120 are activated to detect the leading signals arriving from the emitters 130 or reflected from the markers 140. At S640, it is checked whether this process of transmission by the selected emitters 130 and the sampled sensors 120 has completed and if so, execution continues with S650; otherwise, execution continues with S610.

At S650, the initial sensor(s) 120 to be used and the constraints for the emitters 130 are determined, as described in greater detail herein. It should be appreciated that the USG 110 configured to operate even if not all of the sensors 120 are in contact with the body part and is therefore adapted to select which of the plurality of sensors 120 is best to be used at any given time. This can be changed on an on-going basis as the process continues and as further explained herein.

Figure 9:
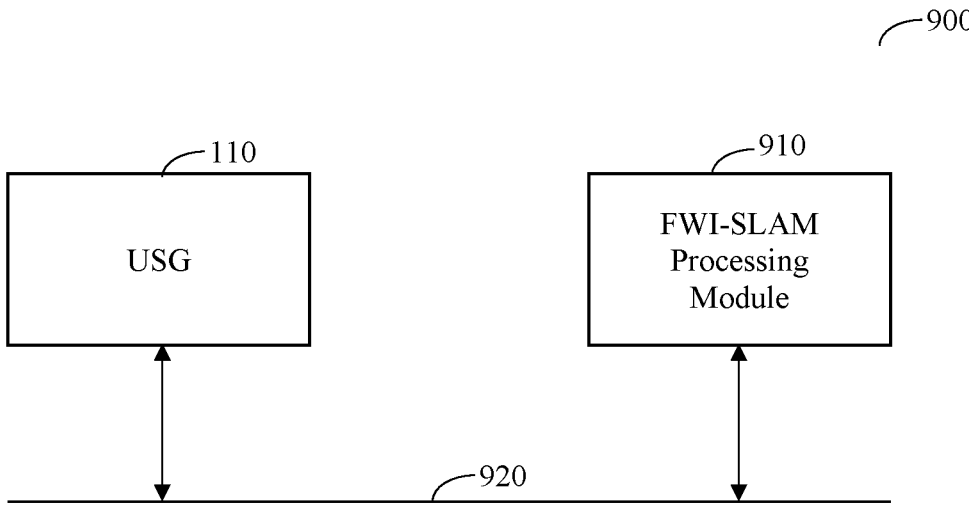
FIG. 9 is a block diagram of a system for processing signals acquired by the ultrasound sensing garment.

At S660, the collected signals may be fully or partially processed, including but not limited to compressing information regarding the signals and sending at S670 the compressed data to an FWI-SLAM processing module, as further discussed in FIG. 9 herein. The initial localization process 600 therefore enables the initial selection of emitter 130 and sensors 120, potentially also making use of the markers 140, to determine those sensors and emitters that are used in the FWI acquisition phase discussed with respect of FIG. 7 herein.

Figure 7:
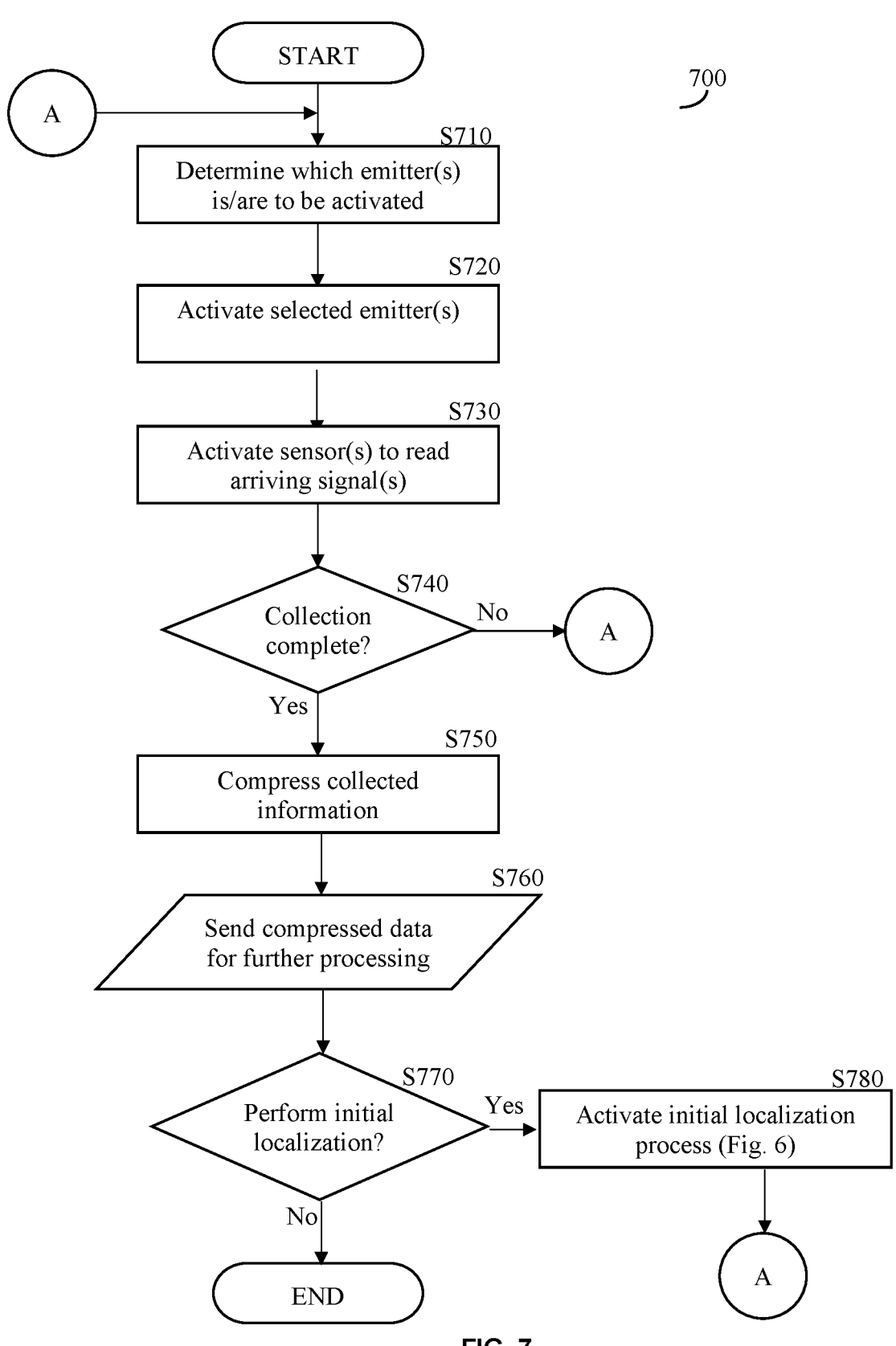
FIG. 7 is a flowchart illustrating a method of full wave inversion (FWI) acquisition according to an embodiment.

FIG. 7 is an example flowchart 700 illustrating a method of FWI acquisition according to an embodiment. Based on the information gathered in the initial acquisition phase, described with respect of FIG. 6, in S710, one or more emitters 130 to be used for image frame capture are determined. In S720, the selected emitters 130 are activated so as to emit an ultrasound signal. In S730, one or more sensors 120 are activated to receive the arriving ultrasound signals. In S740, it is checked if the collection of signals has completed and if so, execution continues with S750; otherwise, execution continues with S710. In S750, the collected signals may be fully or partially processed, including but not limited to compressing information regarding the signals and sending, at S760, the compressed data to an FWI-SLAM processing module, as further discussed in FIG. 9 herein. In S770, it is checked whether the next frame capture requires localization reinitialization and if so, execution continues with S780; otherwise, execution terminates. In S780 the initial localization process described in FIG. 6 is performed, after which execution continues with S710.

Figure 8:
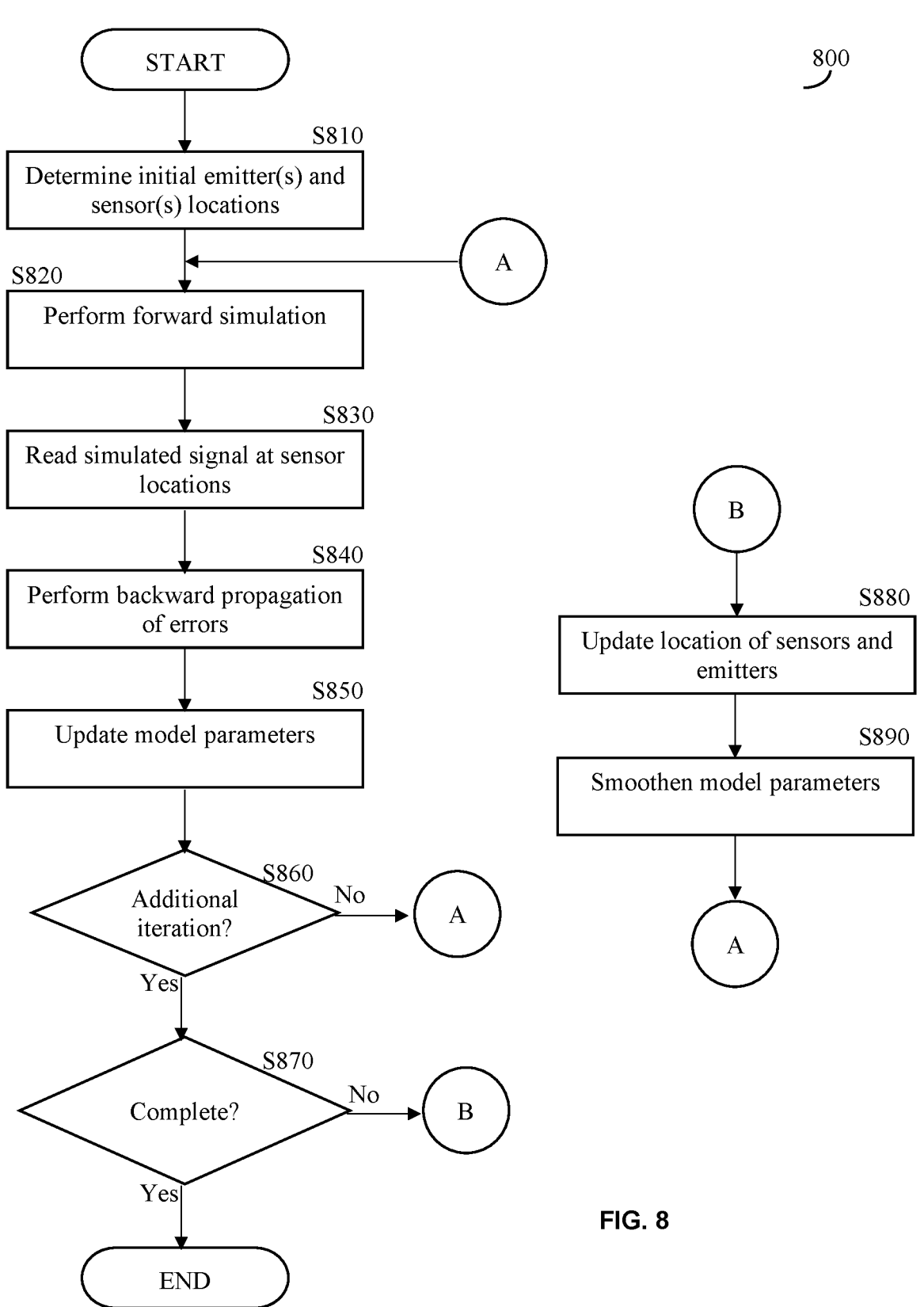
FIG. 8 is a flowchart illustrating full wave inversion with simultaneous localization and mapping (FWI-SLAM) processing of acquired signal according to an embodiment.

FIG. 8 is an example flowchart 800 illustrating FWI-SLAM processing of acquired signal according to an embodiment. At S810, initial sensors 120 and emitters 130 locations are determined based on the information provided as a result of the steps described in FIGS. 6 and 7 herein. At S820, a forward simulation described in more detail herein is performed. At S830, the simulated signal is read at the sensor locations. At S840, backward propagation of errors, as described herein in greater detail, is performed. At S840, the parameters of the model are updated, as further explained herein in greater detail.

At S860, it is checked if an additional iteration of the FWI is required and if so, execution continues with S820; otherwise, execution continues with S870. At S870, it is also checked whether the image processing is complete and if so, execution terminates; otherwise, execution continues with S880. At S880, an update of the locations of sensors 120 and the emitters 130 takes place. At S890, model parameters are smoothened after which execution continues with S820.

FIG. 9 is an example of a block diagram of a system 900 for processing signals acquired by the USG 110. The USG 110 is communicatively connected via a communication connection 920 to an FWI-SLAM processing module. In a typical embodiment, the USG 110 and the FWI-SLAM processing module shall be separate due to the significant computing power necessary to perform at least the tasks described in FIG. 8, and further the imaging resulting therefrom. The communication connection 920 is adapted to deliver large amounts of data from the plurality of sensors 120 for further processing, as well as other information gathered or processed by the electronic circuit 160.

The various embodiments disclosed herein can be implemented as hardware, firmware, software, or any combination thereof. Moreover, the software is preferably implemented as an application program tangibly embodied on a program storage unit or computer readable medium consisting of parts, or of certain devices and/or a combination of devices.

The application program may be uploaded to, and executed by, a machine comprising any suitable architecture. Preferably, the machine is implemented on a computer platform having hardware such as one or more central processing units ("CPUs"), a memory, and input/output interfaces. The computer platform may also include an operating system and microinstruction code. The various processes and functions described herein may be either part of the microinstruction code or part of the application program, or any combination thereof, which may be executed by a CPU, whether or not such a computer or processor is explicitly shown. In addition, various other peripheral units may be connected to the computer platform such as an additional data storage unit and a printing unit. Furthermore, a non-transitory computer readable medium is any computer readable medium except for a transitory propagating signal.

All examples and conditional language recited herein are intended for pedagogical purposes to aid the reader in understanding the principles of the disclosed embodiment and the concepts contributed by the inventor to furthering the art, and are to be construed as being without limitation to such specifically recited examples and conditions. Moreover, all statements herein reciting principles, aspects, and embodiments of the disclosed embodiments, as well as specific examples thereof, are intended to encompass both structural and functional equivalents thereof. Additionally, it is intended that such equivalents include both currently known equivalents as well as equivalents developed in the future, i.e., any elements developed that perform the same function, regardless of structure.

It should be understood that any reference to an element herein using a designation such as "first," "second," and so forth does not generally limit the quantity or order of those elements. Rather, these designations are generally used herein as a convenient method of distinguishing between two or more elements or instances of an element. Thus, a reference to first and second elements does not mean that only two elements may be employed there or that the first element must precede the second element in some manner. Also, unless stated otherwise, a set of elements comprises one or more elements.

As used herein, the phrase "at least one of" followed by a listing of items means that any of the listed items can be utilized individually, or any combination of two or more of the listed items can be utilized. For example, if a system is described as including "at least one of A, B, and C," the system can include A alone; B alone; C alone; 2A; 2B; 2C; 3A; A and B in combination; B and C in combination; A and C in combination; A, B, and C in combination; 2A and C in combination; A, 3B, and 2C in combination; and the like.

What is claimed is:

1. A sensing garment for sensing ultrasound waves from a body part, comprising:

a mesh of fabric adapted to be worn on at least a body part of a wearer;

a plurality of ultrasound sensors, wherein each ultrasound sensor is randomly disposed on the mesh fabric; and a plurality of ultrasound emitters, wherein each ultrasound emitter is randomly disposed on the mesh fabric;

a plurality of markers, wherein each marker of the plurality of markers is randomly disposed on the mesh fabric, and wherein each marker has a reflective pattern that is distinctive from any reflective pattern from any bodily organ or bodily tissue;

wherein each of the plurality of ultrasound emitters emits a wide-angle ultrasound beam;

wherein each of the plurality of ultrasound sensors is adapted to detect ultrasound waves returned from the at least a body part of the wearer and further adapted to transmit at least a portion of the detected ultrasound waves to a controller communicatively connected thereto; and wherein only a portion of the plurality of ultrasound sensors that is larger than a predetermined number of ultrasound sensors is substantially in contact with a skin layer of the at least a body part.

2. The sensing garment of claim 1, wherein the plurality of ultrasound sensors disposed on the mesh fabric are embedded within the mesh fabric.

3. The sensing garment of claim 1, wherein each of the plurality of ultrasound sensors is individually placed with a predetermined distance apart.

4. The sensing garment of claim 1, wherein each of the plurality of ultrasound sensors is at least one of: attached to the mesh fabric, glued to the mesh fabric, and woven within the mesh fabric.

5. The sensing garment of claim 1, wherein each marker of the plurality of markers is at least one of: attached to the mesh fabric, glued to the mesh fabric, and woven within mesh fabric.

6. The sensing garment of claim 1, wherein the detected ultrasound waves are at least one of: a refracted wave and a reflected wave.

7. The sensing garment of claim 1, wherein a number of the plurality of ultrasound sensors exceeds a number of the plurality of ultrasound emitters.

8. The sensing garment of claim 1, wherein the sensing garment is adapted to fit around the at least a body part.

9. The sensing garment of claim 1, wherein the at least a body part is at least one of: a limb, a stomach, a chest, a foot, a hand, a neck, a lower back, an upper back, a torso, a head, and portions thereof.

10. The sensing garment of claim 1, wherein the sensing garment is adapted to provide a predetermined level of flexibility for adaption about the at least a body part.

11. The sensing garment of claim 10, wherein the predetermined level of flexibility for adaption about the at least a body part allows for a predetermined level of motion of the at least a body part with respect to a reference.

12. The sensing garment of claim 11, wherein the reference is any one of: a position of the at least a body part and a position of the at least a body part with respect to another body part.

13. The sensing garment of claim 1, wherein each of the plurality of ultrasound sensors is woven within the mesh fabric at a predetermined density within a garment surface.

14. The sensing garment of claim 1, wherein each of the plurality of ultrasound sensors is woven within the mesh fabric at random positions within a garment surface.

15. The sensing garment of claim 1, wherein each marker of the plurality of markers is composed of a flexible material that is adapted to bend.

16. The sensing garment of claim 1, wherein each marker of the plurality of markers is adapted to enable an initial approximate position of each of the plurality of ultrasound emitters and each of the plurality of ultrasound sensors using an adaptation of full wave inversion with simultaneous localization and mapping.

17. The sensing garment of claim 1, wherein each of the plurality of markers is any one of: a passive marker and an active marker.

18. A system for determining locations of ultrasound sensors disposed onto a mesh fabric of a sensing garment comprising:

a processing unit;

a sensing garment, wherein the sensing garment is adapted to be positioned on at least a body part of a wearer, the sensing garment comprising:

a mesh fabric;

a plurality of ultrasound sensors randomly disposed on the mesh fabric, such that at least a portion of the plurality of ultrasound sensors is substantially in contact with a skin layer of the wearer;

a plurality of wide-angle beam ultrasound emitters randomly disposed on the mesh fabric, wherein each ultrasound emitter is configured to emit a wide-angle ultrasound beam; and a plurality of markers randomly disposed on the mesh fabric, wherein each marker has a reflective pattern that is distinctive from any reflective pattern from any bodily organ or bodily tissue;

a first interface, connected to the processing unit to the plurality of ultrasound sensors and to the plurality of emitters; and a memory, the memory containing instructions that, when executed by the processing unit, configure the system to:

perform at least a simultaneous determination of locations of at least a portion of the plurality of ultrasound sensors and at least a portion of the plurality of ultrasound emitters in relation to at least a body part, wherein the determination comprises simultaneous localization and mapping based at least on soundwaves returned from one or more of the plurality of markers and collected by the at least a portion of the plurality of ultrasound sensors by estimation of physical paths and iteratively minimize misfit between simulated and observed ultrasound signals.

19. The system of claim 18, wherein the plurality of ultrasound sensors disposed on the sensing garment are embedded within a mesh fabric of the sensing garment.

20. The system of claim 19, wherein the plurality of ultrasound sensors is individually placed on the sensing garment and wherein a distance from a neighboring sensor of the plurality of ultrasound sensors is a predetermined distance apart.

21. The system of claim 18, wherein the system is further configured to:

determine a relative position with respect to local coordinates.

22. The system of claim 18, wherein the system is further configured to:

cause one or more of a plurality of ultrasound emitters to generate an ultrasound wave.

23. The system of claim 22, wherein the plurality of ultrasound emitters are disposed on the sensing garment.

24. The system of claim 18, wherein the memory further includes instructions that when executed by the processing unit configure the system to:

perform an adaptation of full wave inversion on signals received from the first interface with respect to the at least a portion of the plurality of ultrasound sensors and to at least a portion of the plurality of markers; and determine for each of the at least a portion of the plurality of ultrasound sensors the sensor localization and mapping.

25. The system of claim 24, wherein the system is further configured to:

iteratively update the position and mapping of each of the plurality of ultrasound sensors; and smoothen model parameters, wherein the model parameters are associated with the full wave inversion.

26. The system of claim 24, wherein each of the plurality of markers is any one of: a passive marker and an active marker.

27. The system of claim 18, wherein the at least a portion of the plurality of ultrasound sensors is above a predetermined number of ultrasound sensors.

28. The system of claim 18, wherein each marker of the plurality of markers is composed of a flexible material that is adapted to bend.

* * * * *